(12) United States Patent
Fiedler et al.

(10) Patent No.: US 9,486,183 B2
(45) Date of Patent: Nov. 8, 2016

(54) APPARATUS FOR COLLECTING DONATED STOOL

(71) Applicant: PL&Y LLC, Arlington, VA (US)

(72) Inventors: Lawrence Michael Fiedler, Boca Raton, FL (US); Peter Salomon, Boca Raton, FL (US); Renato Gross, Auburn, AL (US)

(73) Assignee: PL&Y LLC, Arlington, VA (US)

( * ) Notice: Subject to any disclaimer, the term of this patent is extended or adjusted under 35 U.S.C. 154(b) by 45 days.

(21) Appl. No.: 14/270,336

(22) Filed: May 5, 2014

(65) Prior Publication Data

US 2014/0329273 A1    Nov. 6, 2014

Related U.S. Application Data

(60) Provisional application No. 61/820,092, filed on May 6, 2013.

(51) Int. Cl.
| | | |
|---|---|---|
| *G01N 1/10* | (2006.01) | |
| *C12Q 1/00* | (2006.01) | |
| *G01N 33/48* | (2006.01) | |
| *A61B 10/00* | (2006.01) | |

(52) U.S. Cl.
CPC ................... *A61B 10/0038* (2013.01)

(58) Field of Classification Search
CPC .................. A61B 10/0038; A47K 11/06
See application file for complete search history.

(56) References Cited

U.S. PATENT DOCUMENTS

| | | | | |
|---|---|---|---|---|
| 2,560,199 A * | 7/1951 | Trichel | ............... | A61B 10/0038 4/144.1 |
| 3,754,287 A * | 8/1973 | Taylor | ................... | A47K 17/00 4/661 |
| 4,101,279 A * | 7/1978 | Aslam | ............... | A61B 10/0038 366/314 |
| 4,288,316 A * | 9/1981 | Hennessy | .......... | A61B 10/0038 209/17 |
| 4,318,803 A * | 3/1982 | Holmgren | .......... | A61B 10/0038 206/229 |
| 5,431,884 A * | 7/1995 | McDonough | ...... | A61B 10/0038 209/17 |
| 5,925,250 A * | 7/1999 | Rocha | ................ | A61B 10/0038 209/172 |
| 6,267,753 B1 * | 7/2001 | Kao | .......... | A61J 1/20 604/416 |
| 8,096,955 B1 * | 1/2012 | Vazquez | ................ | A61B 5/207 600/562 |
| 8,394,626 B2 * | 3/2013 | Ramsey | ............... | A61B 10/007 422/400 |
| 8,690,794 B1 * | 4/2014 | Gallardo | ........... | A61B 10/0038 600/562 |
| 2006/0115385 A1* | 6/2006 | Jon Meyer | ......... | A61B 10/0096 422/547 |
| 2008/0213877 A1* | 9/2008 | Hicks | ..................... | B01D 29/01 435/309.1 |
| 2009/0193880 A1* | 8/2009 | Halverson | ................ | G01N 1/18 73/64.56 |
| 2010/0130949 A1* | 5/2010 | Garcia | ................ | A61M 1/0019 604/326 |
| 2010/0278692 A1* | 11/2010 | Chen | ....................... | B01L 3/508 422/420 |
| 2011/0020860 A1* | 1/2011 | Greenwald | ........ | A61B 10/0038 435/34 |
| 2011/0107824 A1* | 5/2011 | Lv | ...................... | A61B 10/0045 73/64.56 |
| 2012/0125125 A1* | 5/2012 | Li | ...................... | A61B 10/0038 73/863 |
| 2014/0017720 A1* | 1/2014 | Sidorsky | ................... | A61J 1/00 435/30 |
| 2016/0066895 A1* | 3/2016 | Schwyn | ............... | A61B 10/007 600/584 |

FOREIGN PATENT DOCUMENTS

WO    WO-2011122949 A1 *  10/2011  ............. A61B 10/00

* cited by examiner

*Primary Examiner* — Susan Su
(74) *Attorney, Agent, or Firm* — Muir Patent Law, PLLC

(57) ABSTRACT

Disclosed are an apparatus for the collection of donated stool, a collection chamber for depositing (or collecting), processing and harvesting stool from a donor and a process for the preparation of a composition comprising donated stool and a pharmaceutically acceptable carrier.

24 Claims, 18 Drawing Sheets

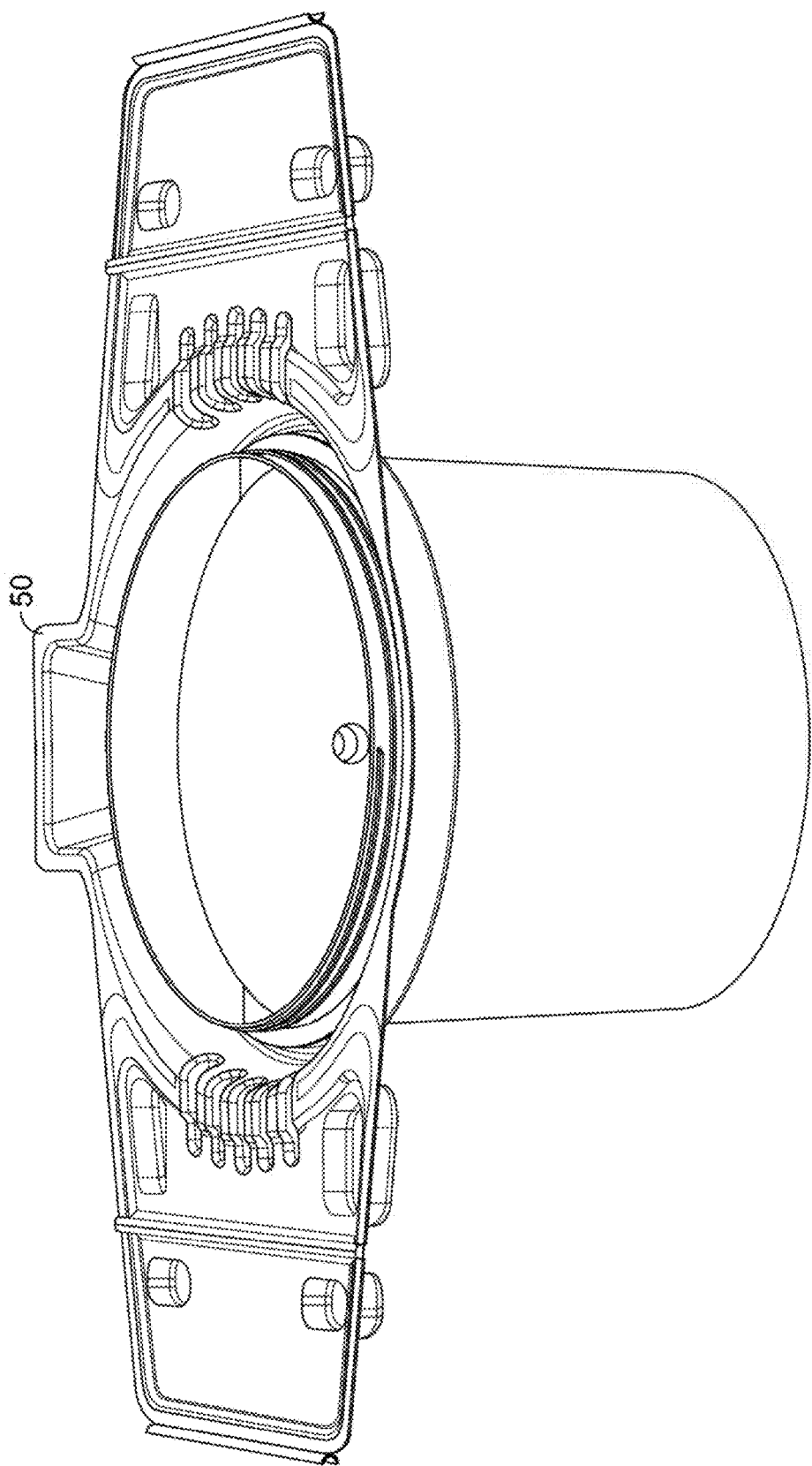

APPARATUS FOR COLLECTING DONATED STOOL

CROSS-REFERENCE TO RELATED APPLICATIONS

This application claims the benefit of U.S. Provisional Application No. 61/820,092, filed on May 6, 2013, the disclosure of which is incorporated herein in its entirety by reference

BACKGROUND

An apparatus is described for collecting, processing and harvesting stool specimens and preparations suitable for fecal transfer regimens and bacteriotherapy.

SUMMARY

A apparatus for the collection of donated stool is disclosed. In certain embodiments, the apparatus comprises a collection chamber and a cradle configured to suspend the collection chamber within a toilet bowl, the collection chamber comprising: (a) a hollow cylindrical drum equipped with a closed bottom and a removable cover to expose an interior of the drum from a top; (b) a divider positioned vertically, horizontally, or diagonally within the drum's interior to divide the drum's interior into at least two compartments, the divider comprising a porous wall or a combination of a porous wall and a solid wall; and (c) one or more ports, which can serve as an inlet, an outlet, or both, provided that at least one of the at least two compartments is fitted with at least one port. In one embodiment, the divider is positioned horizontally, dividing the drum's interior into an upper compartment and a lower compartment, the divider comprising a porous wall. In one embodiment the lower compartment is fitted with a port. The port may comprise a stopcock, such as a two-way stopcock. In one embodiment, an opening of the stopcock is large enough to accommodate a syringe needle or cannula, each having a variety of sizes ranging, for example, from a 20 gauge diameter to a 12 gauge diameter, including 18-, 16- and 14-gauge diameters.

If so desired the apparatus may further be equipped with one or more lead, steel, copper, or other metal balls, a magnetic stirrer bar, or both. The lead balls and/or magnetic stirrer bar can be used to assist in breaking up a stool sample. The magnetic stirrer bar may be located in the lower compartment of the drum and may be responsive to the movement of an external rod revolving about its center axis (i.e., an external electric stirrer). If desired a screen is positioned over an opening of the port, which is directed to the interior of the drum.

In one embodiment the divider comprises a planar sieve having modest to wide openings. The divider may also comprise a planar screen filter having smaller openings relative to the planar sieve.

In an exemplary embodiment of the cradle, a brim extends from an outer portion of the cradle, which brim may then sit over a toilet seat. When positioned inside a toilet the cradle presents a profile similar to one provided by an upside down brimmed hat. The walls of the "hat" may be solid, perforated, or largely open. An exemplary cradle comprises one, two or more U-shaped brackets, for example. Another exemplary cradle comprises a single foldable structure having a flange on which an upper rim of a collection chamber.

In yet another embodiment the divider can be positioned vertically, dividing the drum's interior into a first compartment and a second compartment, the divider comprising a combination of a porous wall and a solid wall. The vertical divider can be configured so that the porous wall is positioned towards the top portion of the drum or conversely towards the lower portion of the drum. Likewise the solid wall can be positioned at either the top or lower portion of the combination divider. As shown in FIG. 6 the first compartment can further comprise a planar semicircular sieve positioned orthogonally (i.e., at a ninety degree angle) to the vertical divider. In one embodiment, the second compartment is fitted with a port, preferably, comprising a two-way stopcock. In one embodiment the top of the first compartment is exposed and the top of the second compartment remains covered. As such, the top cover is divided into two halves. One half can be lifted, removed, or, otherwise, retracted to expose the first compartment from the top, while the other half can remain in position to keep the top of the second compartment covered. After a donor deposits stool into the first compartment, the one half of the top cover can be lowered, replaced, or, otherwise, slid back into place to cover the top of the drum completely.

In still other embodiments the divider comprises a horizontally positioned planar sieve, with a horizontal planar screen filter positioned below the planar sieve but above any port(s). Alternatively, instead of a planar sieve, the divider can be a screen filter having openings smaller than those present in the sieve. Moreover the divider may comprise a lower vertical solid wall and an upper porous wall positioned diagonally from a topmost portion of the vertical solid wall towards a topmost portion of the drum, diving the drum's interior into a first compartment and a second compartment. (See, e.g., FIG. 8) Depicted in this FIG. 8 is a pair of metal balls (made, for example, of lead, steel, copper and the like), which can help break up donated stool to facilitate filtering and collection. The first compartment may further comprise a planar semicircular sieve positioned orthogonally at the topmost portion of the vertical solid wall. The second compartment is fitted in one embodiment with a port comprising, for example, a two-way stopcock.

Conversely the divider may comprise a lower vertical porous wall and an upper solid wall positioned diagonally from a topmost portion of the vertical porous wall towards a topmost portion of the drum, dividing the drum's interior into a first compartment and a second compartment. (See, e.g., FIG. 9) Here too the first compartment may further comprise a planar semicircular sieve positioned orthogonally at the topmost portion of the vertical porous wall, and the second compartment may be fitted with a port, for example, comprising a two-way stopcock.

Also described herein is a collection chamber for depositing, processing and harvesting stool from a donor comprising: (a) a hollow cylindrical drum equipped with a closed bottom and a removable cover to expose an interior of the drum from a top; (b) a divider positioned vertically, horizontally, or diagonally within the drum's interior to divide the drum's interior into at least two compartments, the divider comprising a porous wall or a combination of a porous wall and a solid wall; and (c) one or more ports, which can serve as an inlet, an outlet, or both, provided that at least one of the at least two compartments is fitted with at least one port.

A process is also provided for the preparation of a composition comprising donated stool and a pharmaceutically acceptable carrier, the process comprising: (a) mixing stool provided by a donor and an effective amount of a pharmaceutically acceptable carrier in a collection chamber equipped with (i) a removable cover that is closed, and (ii) one or more ports, which can serve as an inlet, an outlet, or both, to provide a stool slurry; and (b) harvesting the stool slurry by utilizing the one or more ports, while keeping the removable cover closed.

Additional embodiments are disclosed in the figures and detailed description that follows.

BRIEF DESCRIPTION OF THE DRAWINGS

FIGS. 5A-5C show additional exemplary views of the apparatus of FIG. 3, depicting different portions of and configurations of the apparatus of FIG. 3, according to certain exemplary embodiments;

DETAILED DESCRIPTION

Figure 1:
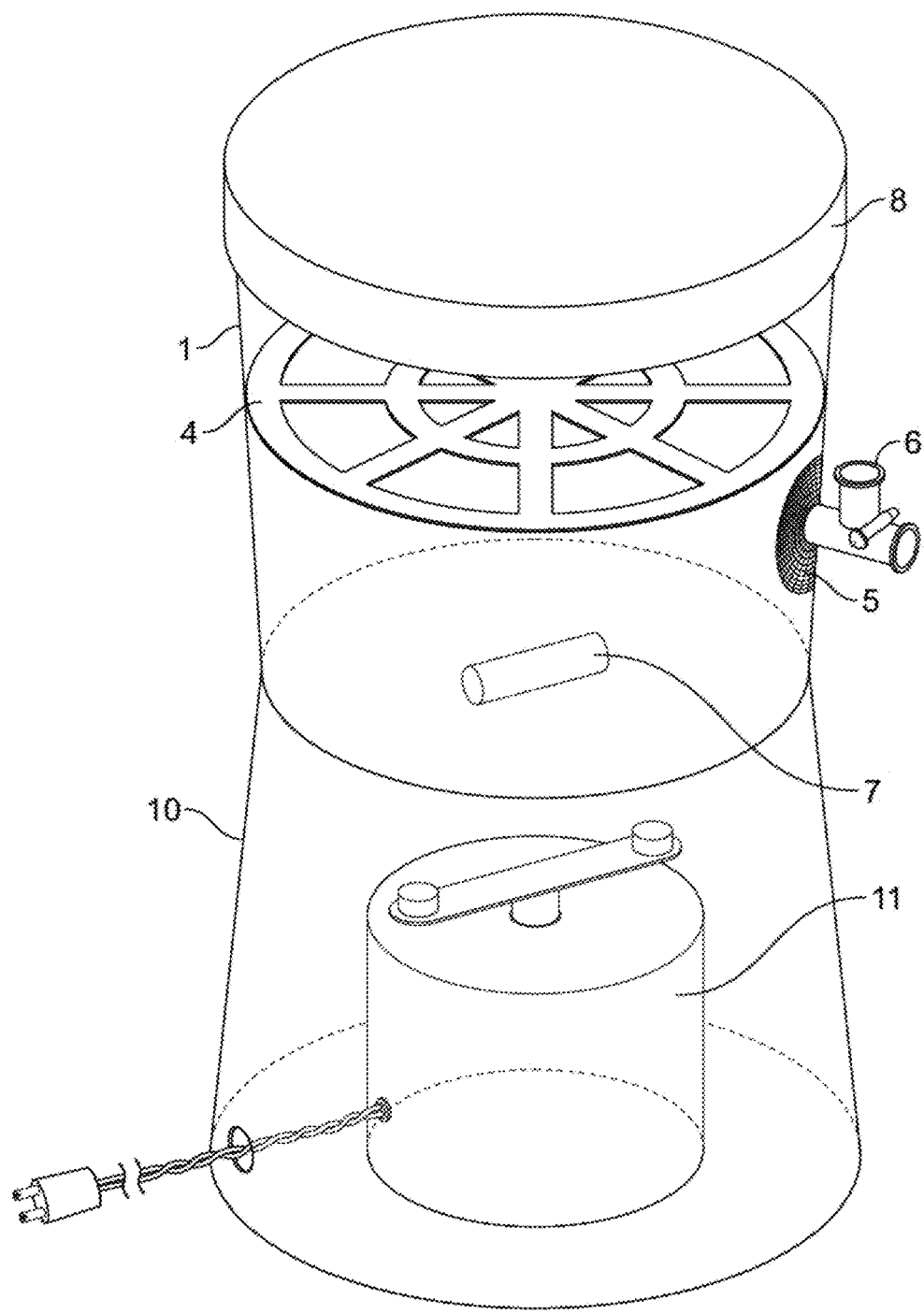
FIG. 1 depicts an exemplary apparatus including a collection chamber (1), a removable top cover (8), a planar sieve platform (4), an optional magnetic stirrer bar (7), a port (6) comprising a stopcock, an optional screen (5) positioned over an opening of the port (6) and an optional magnetic stirring platform (11), including a stirring platform cover (10), according to one exemplary embodiment.

The present disclosure now will be described more fully hereinafter with reference to the accompanying drawings, in which various embodiments are shown. The invention may, however, be embodied in many different forms and should not be construed as limited to the embodiments set forth herein. In the drawings, the size and relative sizes of layers and regions may be exaggerated for clarity. Like numbers refer to like elements throughout.

As used herein, the term "and/or" includes any and all combinations of one or more of the associated listed items and may be abbreviated as "/".

It will be understood that, although the terms first, second, etc. may be used herein to describe various elements, these elements should not be limited by these terms. Unless indicated otherwise, these terms are only used to distinguish one element from another. For example, a first chip could be termed a second chip, and, similarly, a second chip could be termed a first chip without departing from the teachings of the disclosure.

As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

It will be understood that when an element is referred to as being "connected" or "coupled" to or "on" another element, it can be directly connected or coupled to or on the other element or intervening elements may be present. In contrast, when an element is referred to as being "directly connected" or "directly coupled" to another element, there are no intervening elements present.

The exemplary views shown in the drawings may be modified depending on manufacturing technologies and/or tolerances. Therefore, the disclosed embodiments are not limited to those shown in the views, but include modifications in configuration formed on the basis of manufacturing processes. Therefore, regions exemplified in figures have schematic properties, and shapes of regions shown in figures exemplify specific shapes of regions of elements, and the specific properties and shapes do not limit aspects of the invention.

Spatially relative terms, such as "beneath," "below," "lower," "above," "upper" and the like, may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

What follows is a description of the various components and examples of apparatuses for collecting a stool sample, according to various embodiments. Exemplary manufacturing methods for forming these example apparatuses are also described. In addition, exemplary processes for collecting and examining stool samples using these apparatuses are described. Certain labels or label numbers are used in the following descriptions as examples only, and though a term may be described in connection with a particular numbered item of a particular figure, that term may generally refer to items in the various figures.

Figure 4:
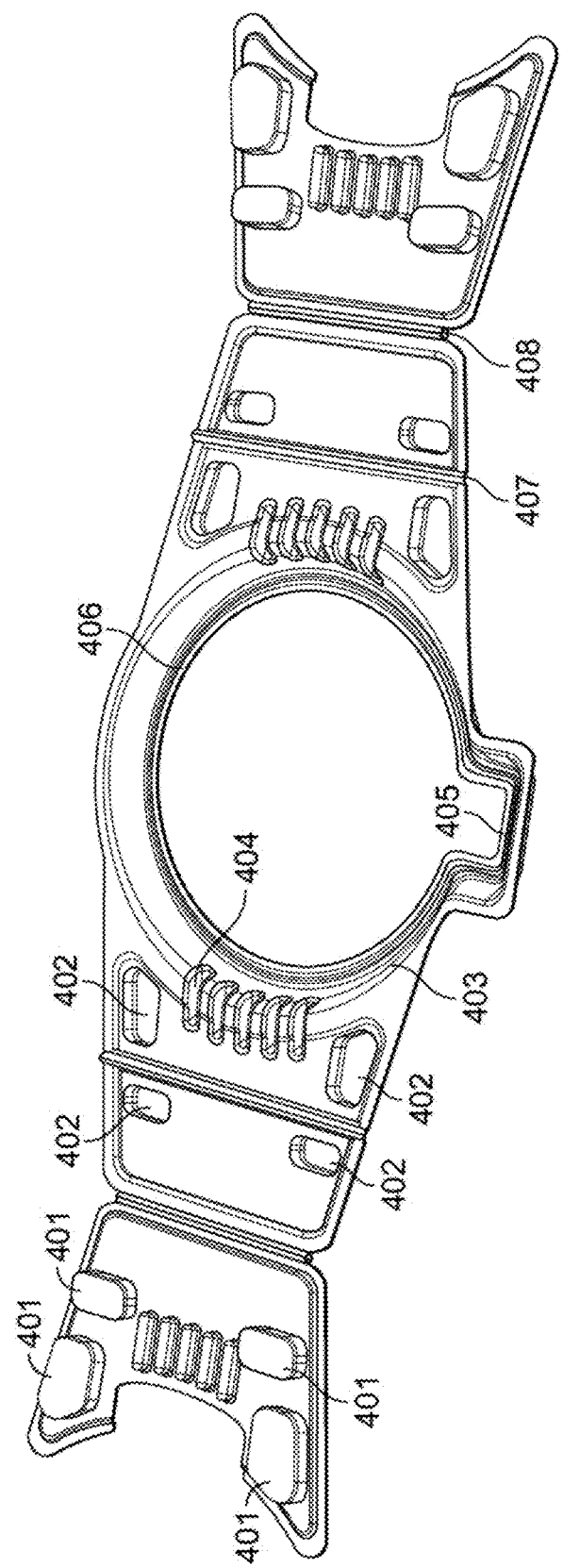
FIG. 4 illustrates an exemplary top view of the cradle of FIG. 3, according to one exemplary embodiment.
Figure 5B:
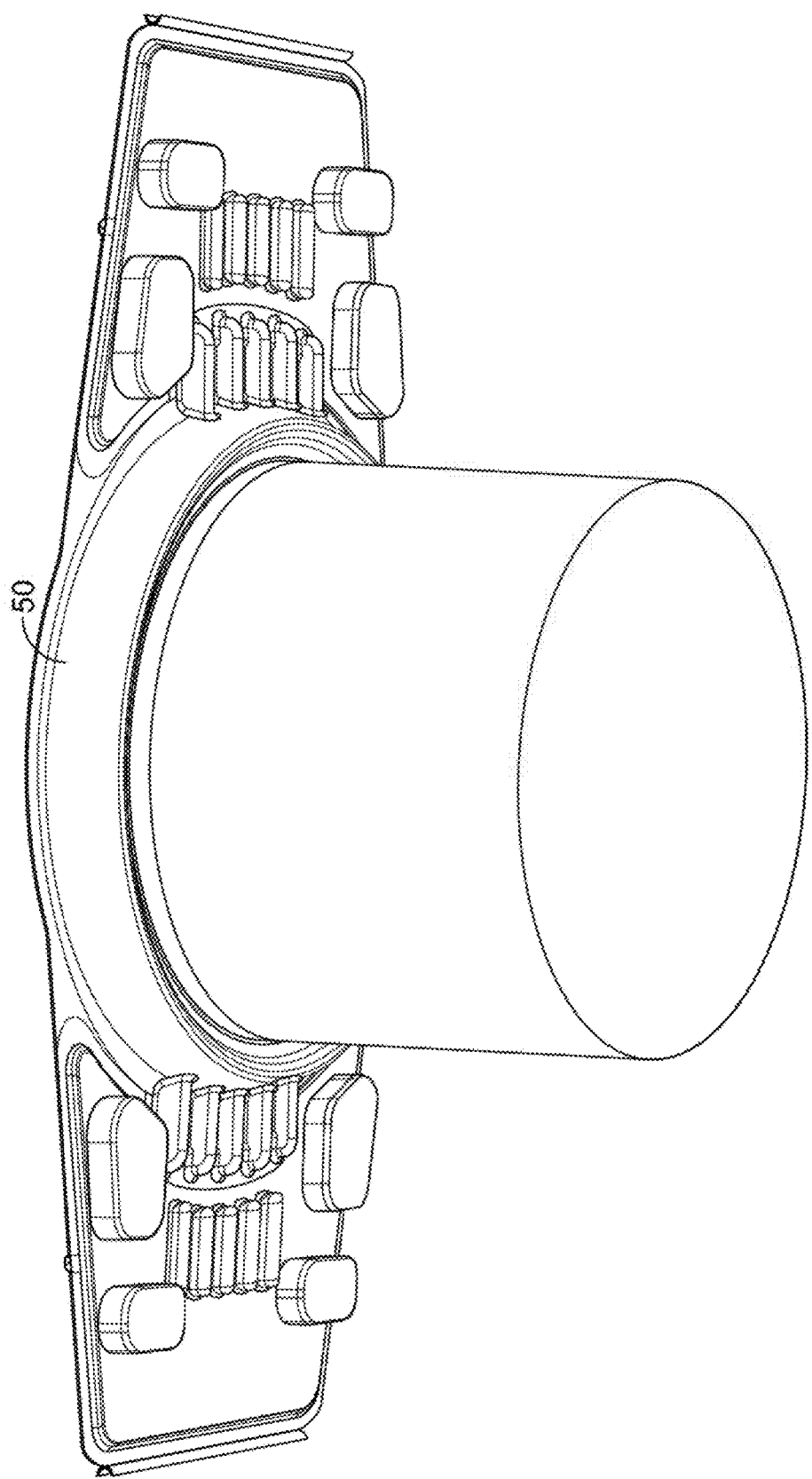
Figure 5C:
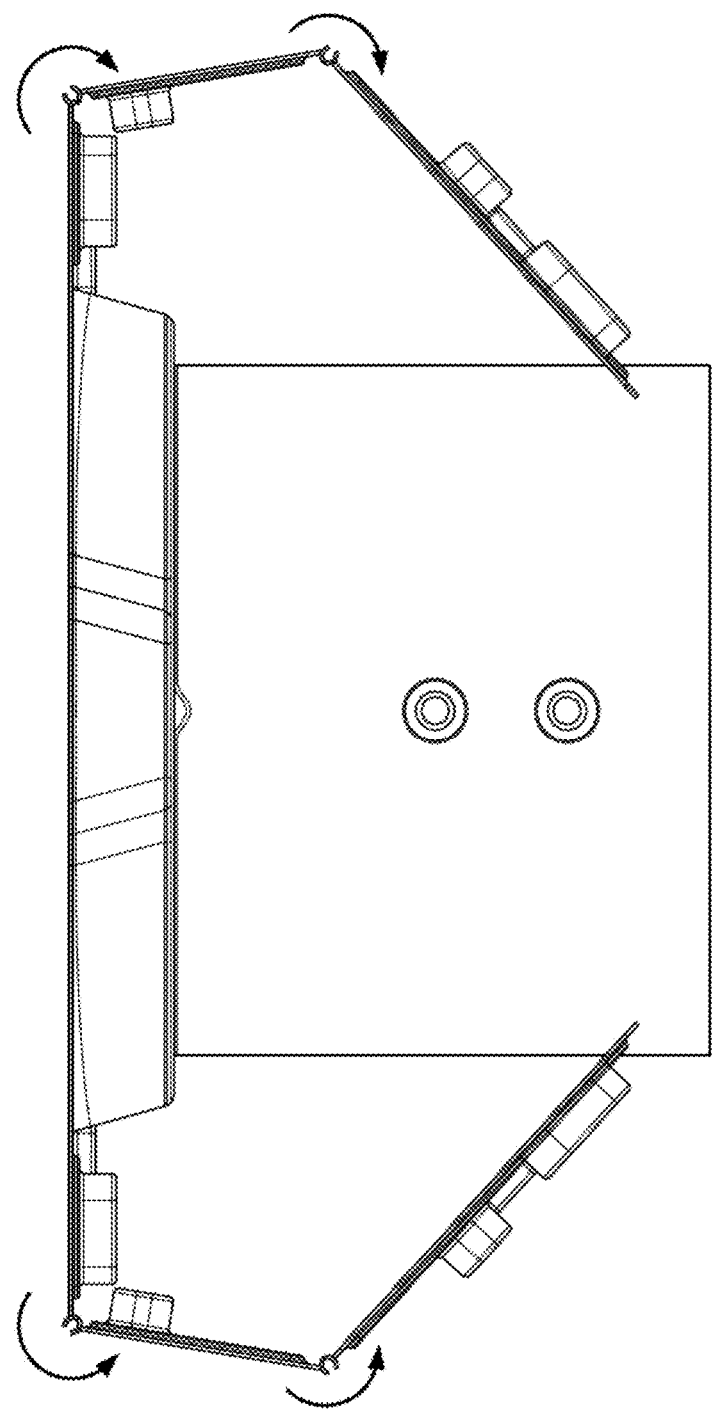

As one example, an apparatus includes a collection chamber (e.g., 1, shown in various figures), which is placed in a collection chamber cradle (an example of which is shown in FIG. 4 alone and FIGS. 5A-5C together with a collection chamber). The cradle may also be referred to herein as a container holder or container support, or a toilet mount. The cradle is placed across the toilet seat, and the collection chamber is placed inside the cradle. The donor defecates into a portion of the collection chamber. The collection chamber is then removed, and the collected stool is processed as discussed in further detail, below.

Figure 6:
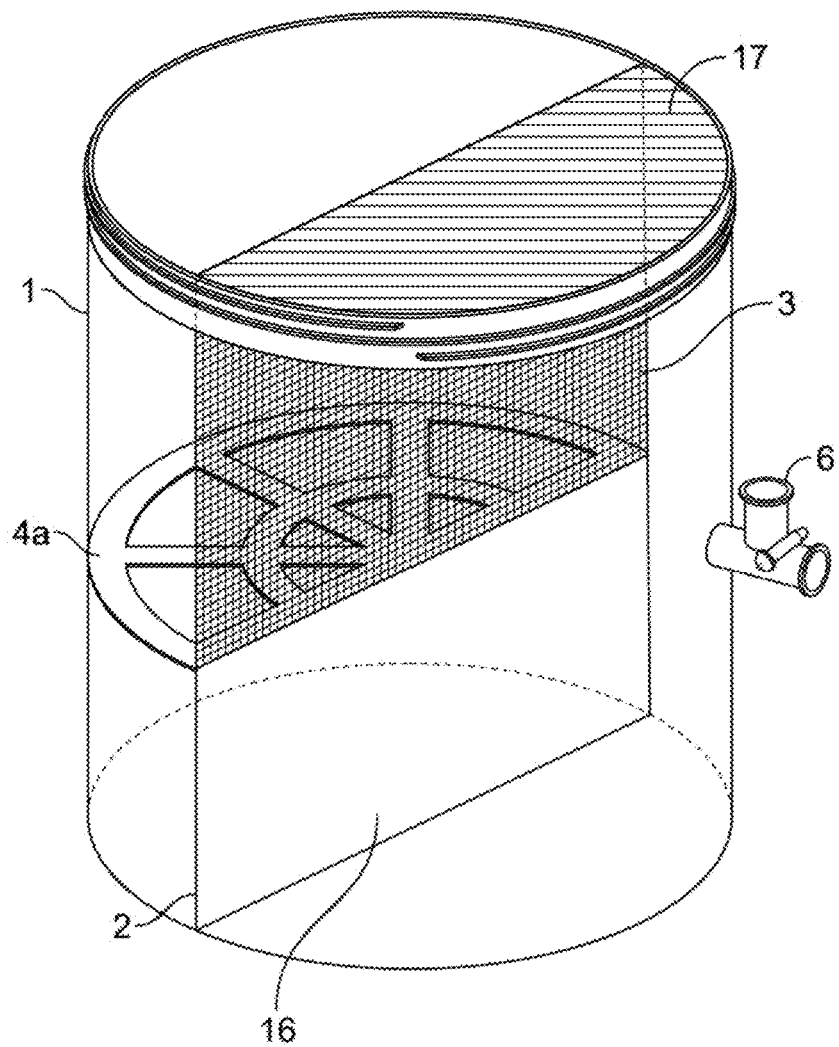
FIG. 6 depicts an exemplary apparatus equipped with a collection chamber (1), a vertical divider (2) comprising a top porous wall comprising a screen filter (3) and a bottom solid wall (16), and a planar semicircular sieve (4a) positioned orthogonally to the vertical divider (2) at a junction of the bottom and top walls and at least one port (6), according to one exemplary embodiment. The vertical divider may include a flap (17) covering one compartment of the collection chamber when the vertical divider is positioned vertically in the collection chamber.

As can be seen from the illustrations, in certain embodiments, a dividing wall (e.g., 2, FIG. 6; 2a, FIG. 8; 2b, FIG. 9, 102, FIG. 10A) is positioned in the interior of the collection chamber vertically, horizontally, or diagonally. The divider is used to separate an area or compartment of the collection chamber, which is used to receive the stool specimen (e.g., a collection portion), from another area or compartment of the collection chamber, which is used to collect broken down/filtered stool, for example, for administration to a patient in need thereof (e.g., an extraction portion). In some embodiments the divider is comprised of a planar sieve (e.g., 4, FIGS. 1 and 7; 4a of FIG. 8). In other embodiments the divider is comprised of a combination of a porous wall (e.g., 3, FIG. 6; 3a of FIG. 8; 3b of FIG. 9) and a solid wall (e.g., 16, FIG. 6; 16a of FIG. 8; 16b of FIG. 9). In some embodiments, a divider may include only a porous wall throughout all or most of the height of the porous wall (e.g., 107, FIGS. 10A and 10C). An exemplary dividing wall 2, partial lid 17 for covering an extraction portion of the collection chamber, and sieve platform 4a, can also be seen in FIG. 6.

In certain instances the porous wall is referred to as a dividing wall screen filter, or simply as a filter (e.g., see FIGS. 6A, 8, 9, 10A, and 10C). The filter may separate the collection portion of the collection chamber from the extraction portion of the collection chamber. In certain embodiments, the screen filter allows for passage of only smaller particles of stool from a first compartment (e.g., collection portion) of the collection chamber where the stool is deposited/collected to a second compartment (e.g., extraction portion) of the collection chamber where the filtered stool mixture/suspension is harvested.

In certain embodiments, a "whole" sieve platform (e.g., 4, FIG. 7) or a "half" sieve platform (e.g., 4a, FIGS. 6, 8 and 9) can act as a false bottom to receive donated stool. The perforations, openings, or otherwise gaps in the sieve platform allow only softer, more easily filterable, stool to fall through to a second compartment of the collection chamber (in one embodiment a lower portion of the collection chamber, but, in another embodiment, an adjacent compartment) in which the stool can be recovered as a slurry, a suspension, a solution, or otherwise a mixture or combination comprising stool and a pharmaceutically acceptable carrier, such as a saline solution. However, the sieve platform, whether whole or half, need not be included in the collection chamber, and may be absent in certain embodiments.

Figure 10A:
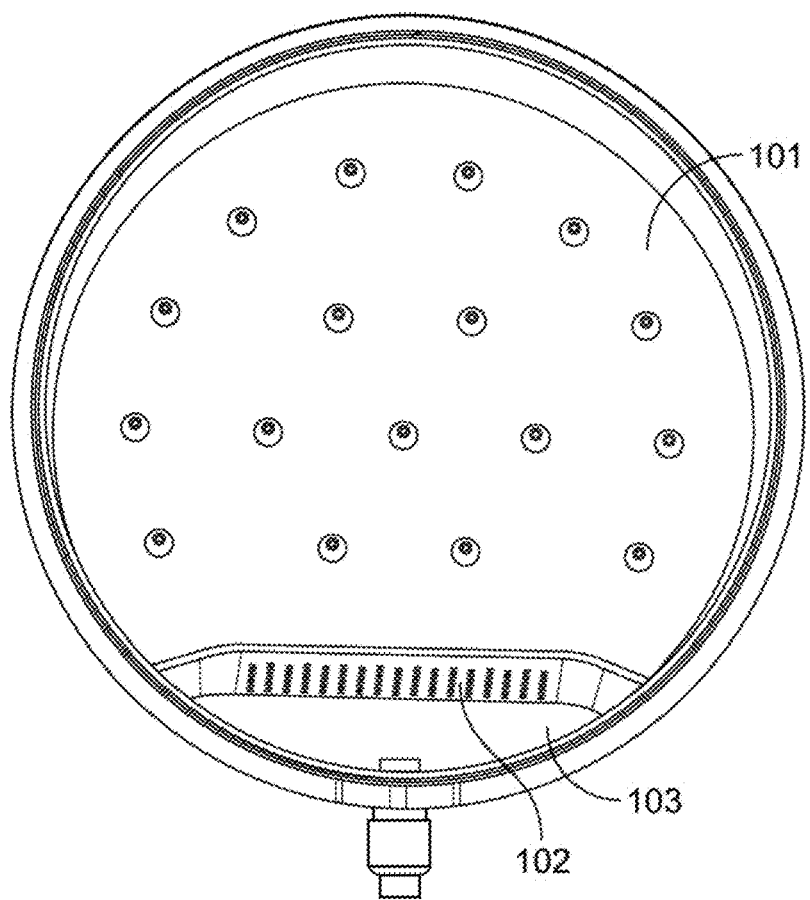
FIGS. 10A-10G depict exemplary views of a collection container including a deposit chamber (101), a filter (102), an extraction chamber (103), agitators (104), a locator for a cradle (105), a port (106), an extraction chamber lid (107), a lip (108), a snap-on portion (109), notches (110), a toilet mount locator (111), and fill lines (112) according to certain exemplary embodiments.
Figure 10B:
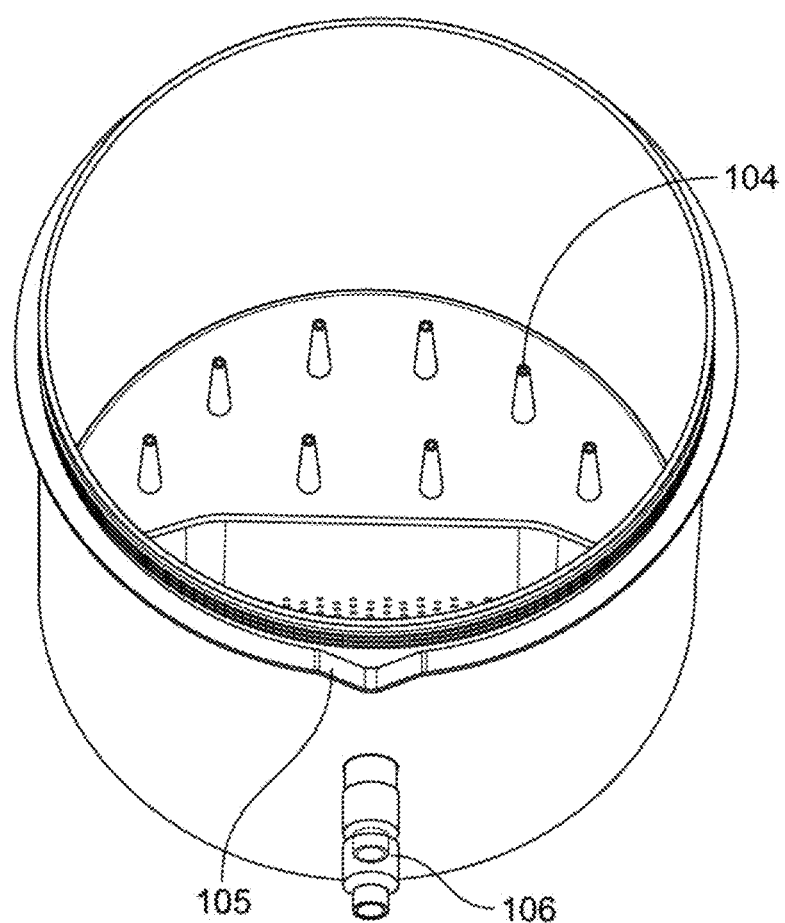
Figure 10C:
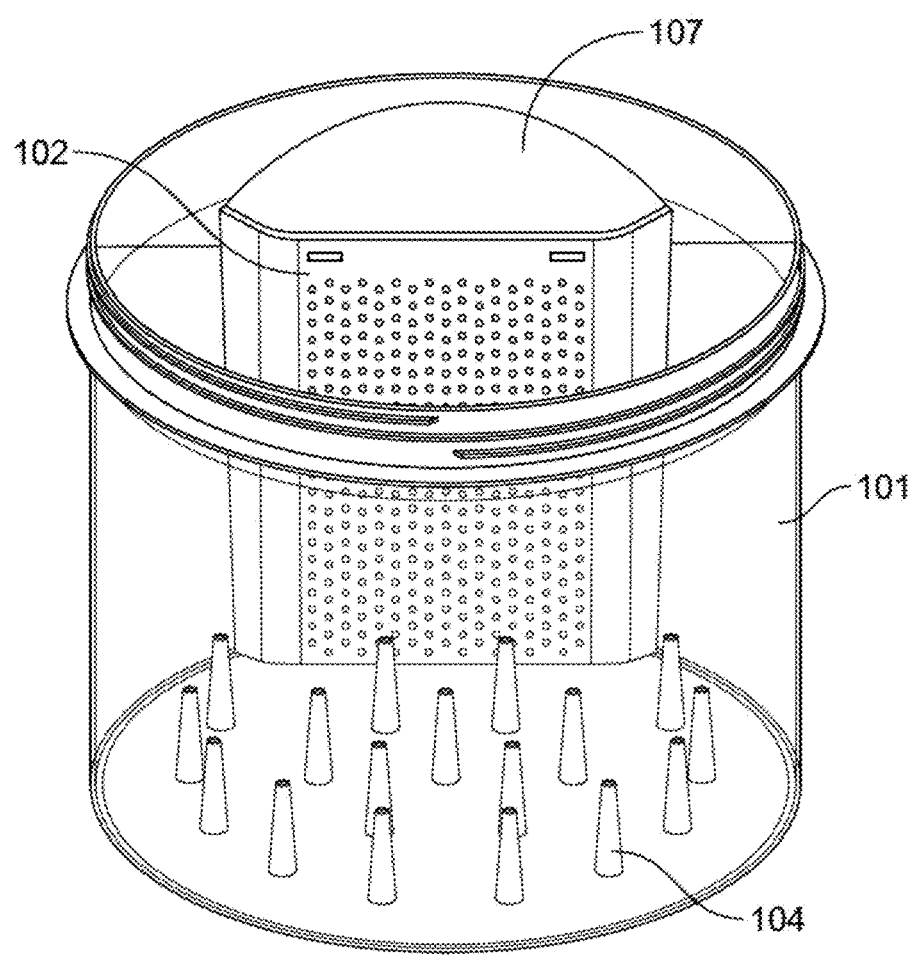
Figure 10D:
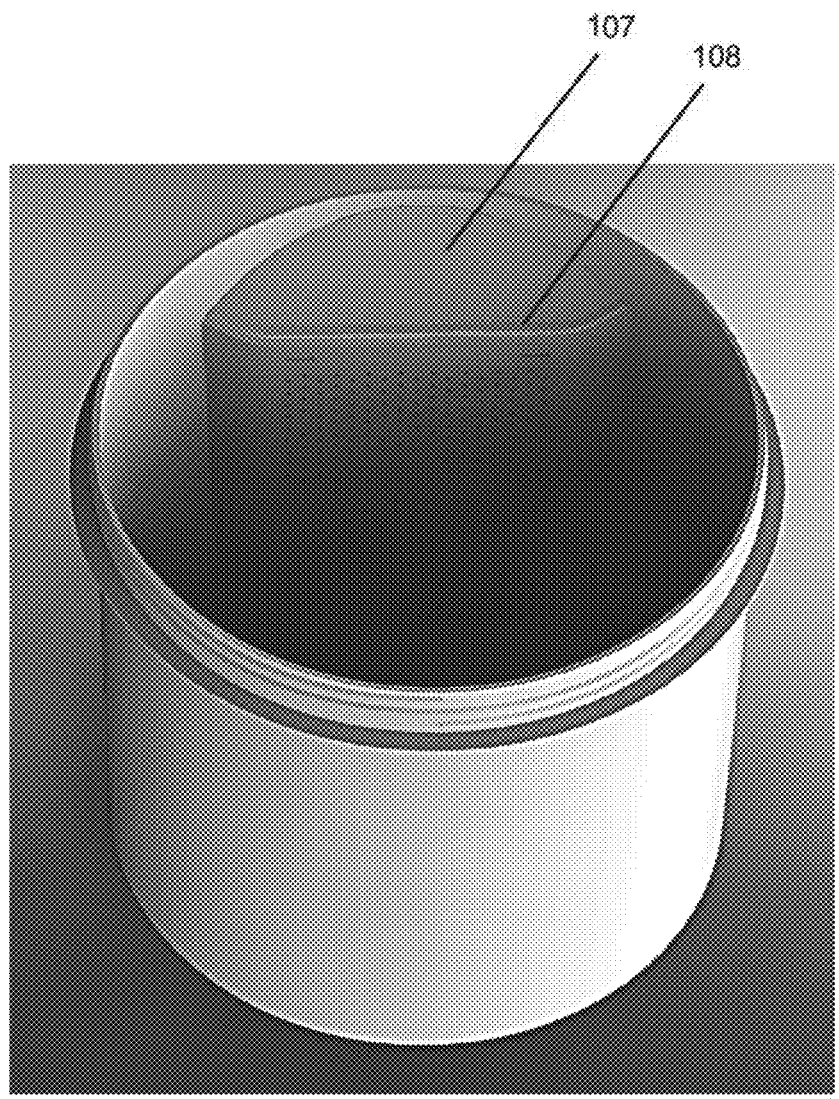
Figure 10E:
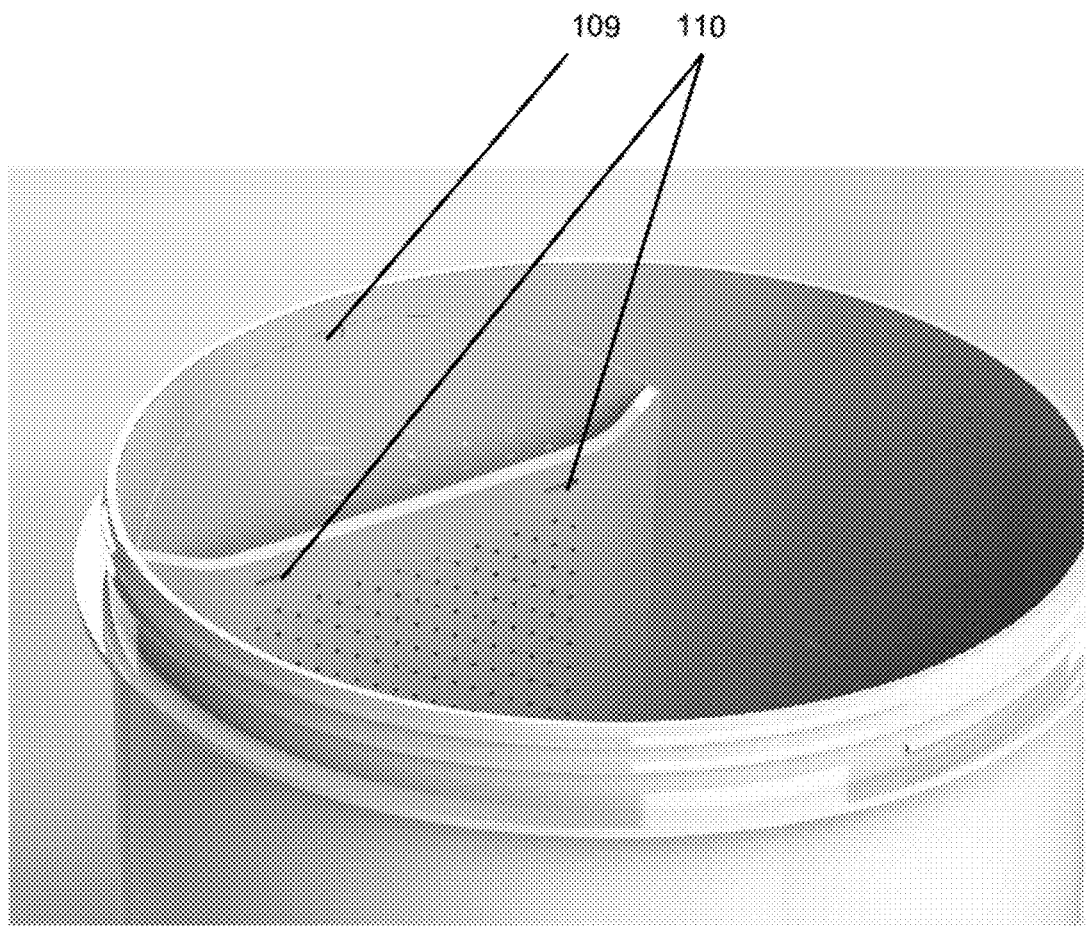
Figure 10F:
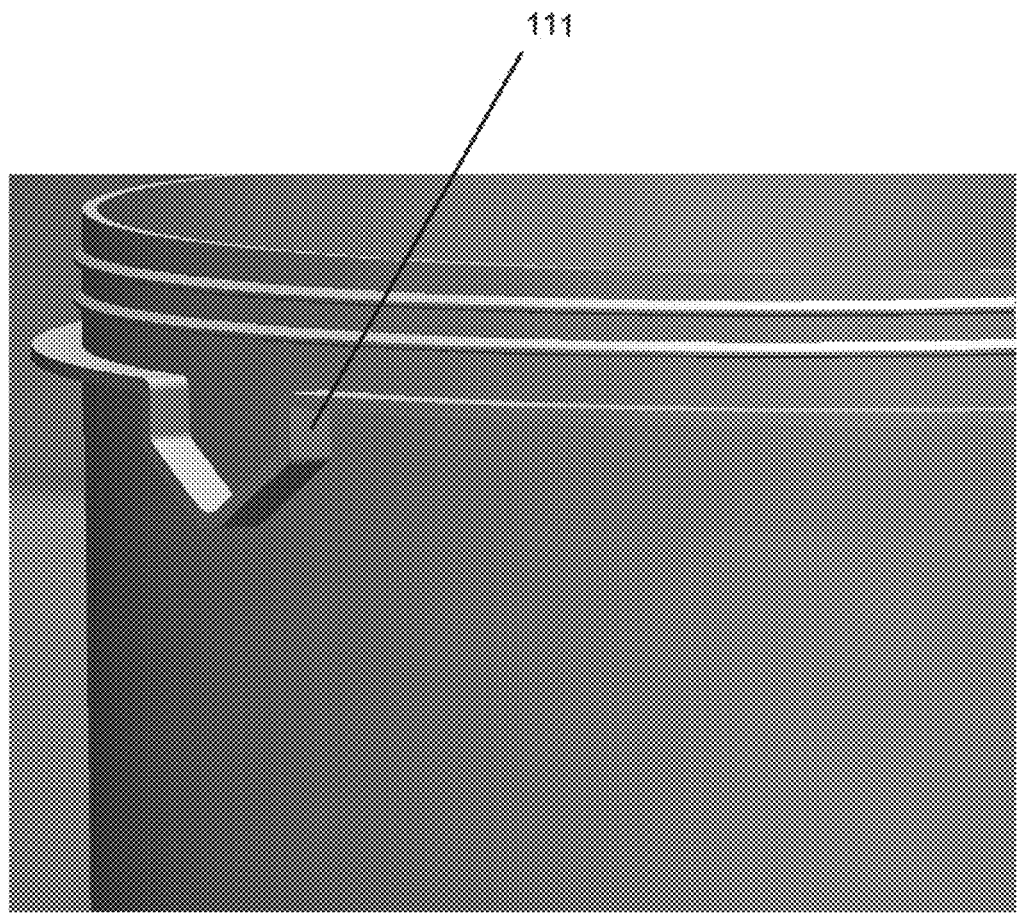
Figure 10G:
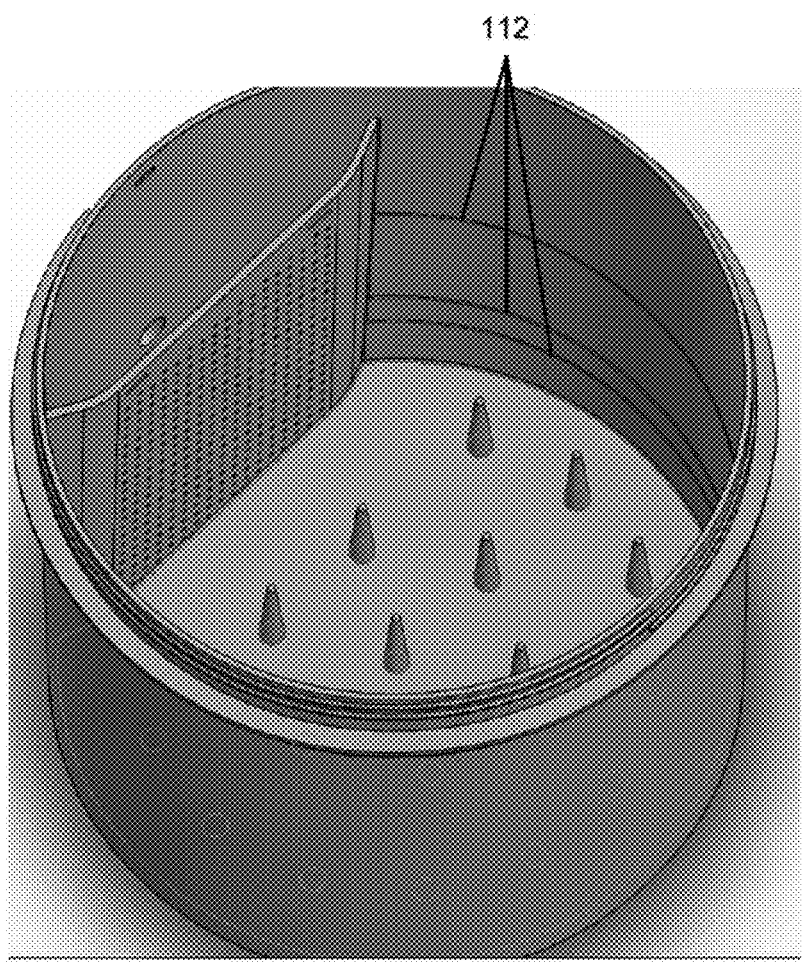

In yet another embodiment a circular, semicircular, hemispherical, domed, or otherwise "half-sphere" screen filter (e.g., 5, FIG. 1) can be positioned about an opening of a port or inlet/outlet, helping to prevent clogging of the opening while allowing smaller solid particles to pass through. Another example of a filter is shown in FIGS. 10A through 10C. In these examples, a filter can include a plurality of slots or holes through which certain sized solid particles can pass through, and the filter may have a flat shape for the portion that includes the holes or slots. However, a filter or porous wall used to separate the collection portion from the extraction portion of the various exemplary collection chambers described herein can take on various shapes, and should not be limited by the examples described herein.

With reference to a port, inlet, or outlet, as the case may be, a cap may be fitted over an opening thereof, or a septum that can be pierced, or a stopcock can be utilized to seal or expose interior contents of the collection chamber to an exterior atmosphere. In various embodiments, the stopcock (e.g., 6, as shown in various figures; 106 as shown in FIG. 10B) comprises a two- or three-way stopcock that allows for the introduction of saline, water, or some other pharmaceutically acceptable carrier into the interior of the collection chamber, as well as the removal of a resulting mixture comprising a stool sample. In addition, a separate valve (e.g., 83, FIG. 2) in the lid of the collection chamber may be used to introduce saline, water, or other carriers into the interior of the collection chamber, and/or as a vent.

In one embodiment a stirrer, such as a magnetic stirrer can be included in the collection chamber (e.g., 7, FIG. 1) to facilitate mixing of the donated stool and a suitable carrier. Likewise metal balls (e.g., 13, FIG. 8) can be present inside the collection chamber, once more to facilitate dissolution or suspension of a stool sample. It is important to note that any means for mixing the contents of the collection chamber, without opening the same, is contemplated in the apparatus described herein. In FIG. 2 an exemplary cover is shown, which seals the collection chamber after donated stool has been deposited by a donor. It is contemplated that once sealed, the collection chamber remains sealed throughout the remaining steps of agitating the collection chamber's contents and harvesting same into a convenient container (e.g., a large syringe) for delivery to a recipient. As shown in FIG. 2, the cover may include a top 81 and a bottom 82. The lid may include a valve 83, such as described above. The lid may also include a thread 85 and seal 86 to achieve a tightly sealed chamber. Other devices may be used, however, for securely closing and sealing the collection chamber. In one embodiment, the lid further includes a cross rib 84 to allow for easy securing and removal of the lid.

As depicted in FIGS. 3, 4, and 5A-5C, a suitable holder, which may be referred to herein as a cradle, can be envisioned by which the collection chamber can be held, and suspended in a toilet, allowing a donor to deposit a stool specimen into the collection chamber in relative comfort. An exemplary cradle is equipped with a brim (50, FIGS. 5B, 5C), which facilitates the positioning of the cradle on a toilet seat. In one embodiment, the cradle includes a single piece that is foldable, to allow for strengthened support as well as compact shipping. An example of a device for holding the collection chamber in place in a toilet is further described as a toilet mount, and is discussed further in connection with FIGS. 3, 4, and 5A-5C.

Figure 3:
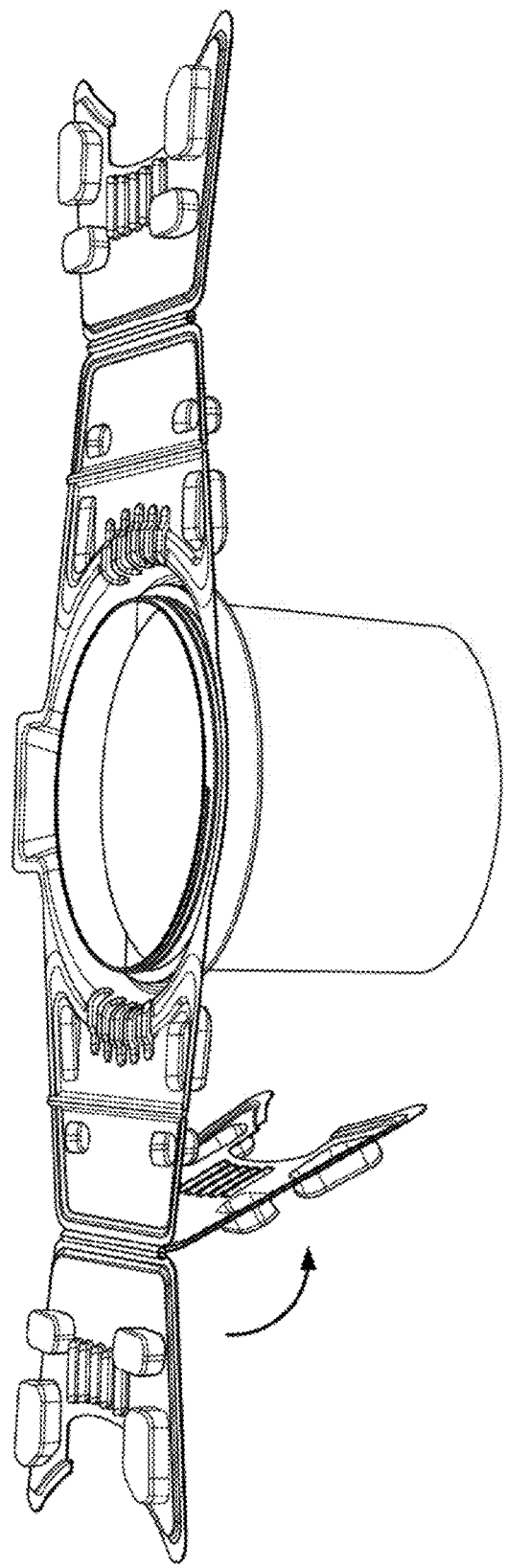
FIG. 3 illustrates an exemplary apparatus including a collection chamber connected to a cradle, according to one exemplary embodiment.

As shown in FIGS. 3 and 4, in one embodiment, a toilet mount may be formed of a plurality of foldable portions and a mounting portion on which the collection chamber may be mounted. For example, the toilet mount may have a wing structure, including two wings 404 that extend from the mounted collection chamber to either side of a toilet. In one embodiment, each wing includes two hinges. A first hinge 407 may be used for compact shipping (see, e.g., FIG. 5C, showing an exemplary shipping position of the wings). A second hinge may be used when the apparatus is being used to collect a stool sample. For example, in one embodiment, the wing is folded over at the second hinge when used, which provides ample support to support the weight of the collected stool sample. The folded wing may be snapped into place using, for example, snap on prongs 401 and snap on sockets 402.

The toilet mount of FIGS. 3, 4, and 5A-5C further includes a receptacle portion 403 for receiving a collection chamber. The receptacle portion 403 may include, for example, a flange 406 on which the container sits, and may also include a notch 405, or other locator to allow the container to be easily mounted on the toilet mount. In certain embodiments, the collection chamber may be snapped or twisted into place after being positioned in the receptacle portion 403 in order to secure the connection with the toilet mount.

FIG. 3 shows an example of outer portions of the wings being folded under the inner portions in order to use the apparatus for stool collection. FIGS. 5A and 5C show an overhead and underneath view of the wings after being folded, in a position ready for use. The snap on geometry and location together with the rib geometry and location, along with a double wall thickness (due to the folding) create a sturdier wing structure for the toilet mount.

In certain embodiments, the collection chamber may be permanently affixed to the toilet mount, so that the two parts arrive at a donor and are shipped from the donor in a simple, ready-to-use manner In other embodiments, the collection chamber may be mountable and removable from the toilet mount, so that the toilet mount need not be shipped after use.

Although not shown, in one embodiment, the cradle may comprise supporting brackets, such as a pair of crossed, U-shaped brackets, which extend beneath the collection chamber and attach to the brim.

Figure 2:
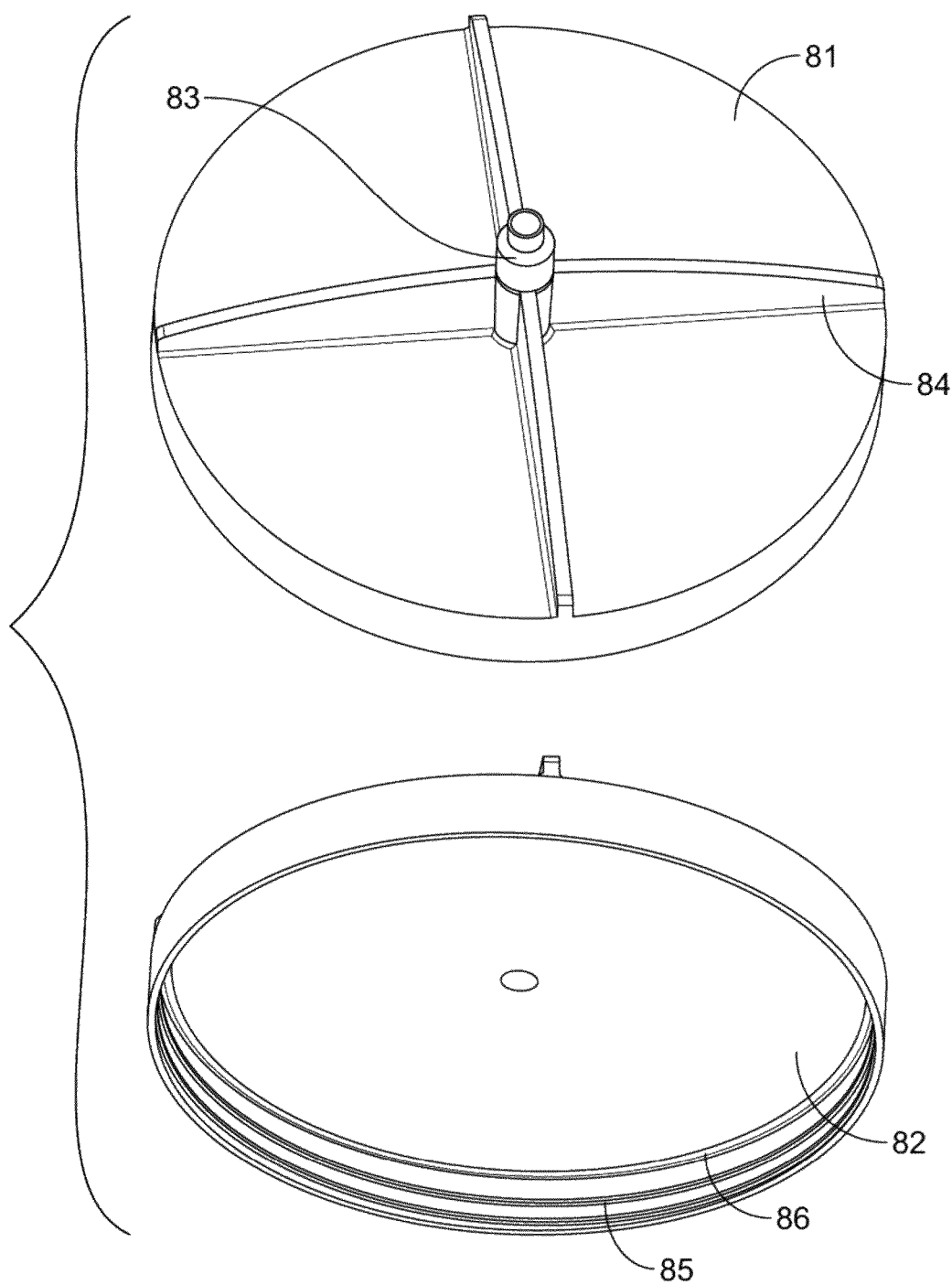
FIG. 2 illustrates top and bottom views of an exemplary top cover (8) for the apparatus of FIG. 1, according to one exemplary embodiment.

In continuing the description of an exemplary use of the apparatus for collecting stool, a stirring platform cover (e.g., 10, FIG. 1) is placed over a magnetic stirrer platform (e.g., 11, FIG. 1). The sealed collection chamber is placed on the platform cover in anticipation of turning on the magnetic stirrer platform to mix the fecal specimen with a suitable carrier.

Figure 7:
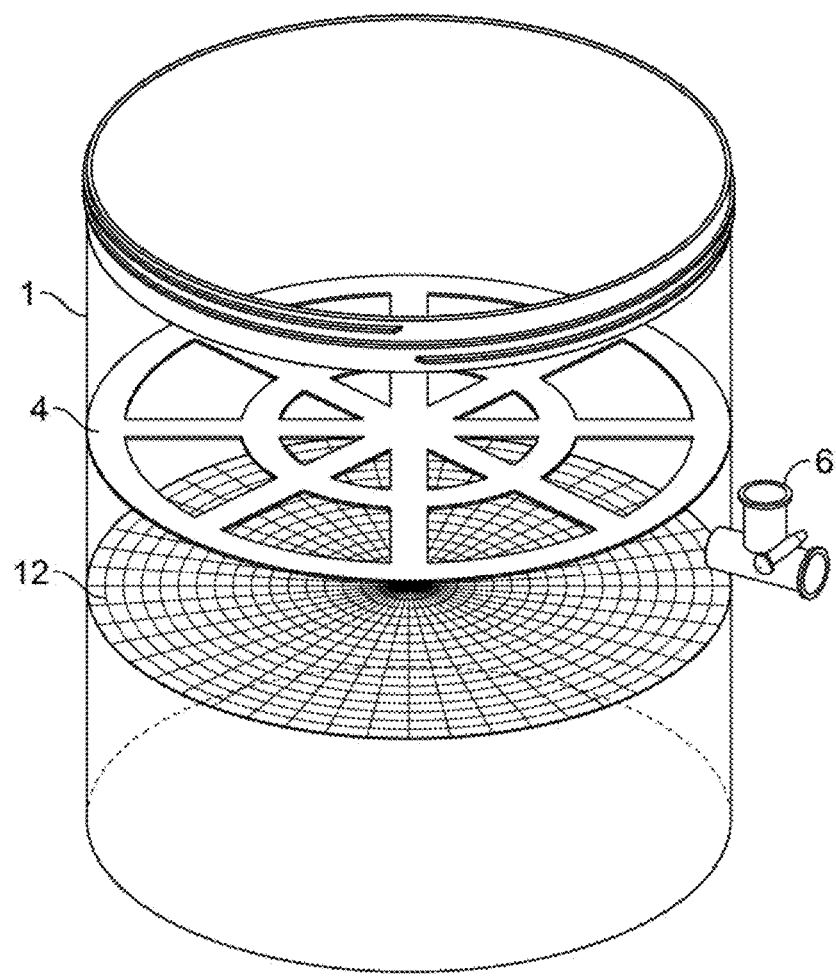
FIG. 7 shows an exemplary collection chamber (1) equipped with a planar sieve platform (4) positioned above a planar screen filter platform (12) and including a port (6), according to one exemplary embodiment.

In certain embodiments of the collection chamber described herein, tandem platforms are positioned within the collection chamber, including a "whole" sieve platform (e.g., 4) and a screen filter platform (e.g., 12), as shown, for example in FIG. 7. Donated stool falls through the sieve platform and directly onto the screen filter platform, which, in turn, allows passage of only small particles thereby preventing clogging of the two way stopcock (e.g., 6, FIG. 7).

An additional example of a collection chamber is shown in FIGS. 10A-10C. As can be seen in these figures, this exemplary collection chamber includes a collection portion (also referred to as a slurry chamber) separated from an extraction portion by a porous wall 102, which serves as a filter. The collection portion may include agitators 104, which in one embodiment, are spiked-shaped protrusions extending from a bottom of the collection portion. The collection chamber may include a port 106 and a notch 105, as described previously. In one embodiment, the notch may have a shape that easily assists in aligning the collection chamber with the toilet mount, such as a V shape, arrowhead shape, or the like, when viewed from a side of the collection chamber. In addition, the extraction portion of the collection chamber may include a lid 107. In one embodiment, the lid 107 is slanted toward an inside of the collection chamber. The lid may be securely fastened to the top of the extraction portion. For example, in one embodiment, the lid may connect to the body of the collection chamber using, for example, notches near the top of the porous wall 102 and a snap-on notch on the rim of the collection chamber. The lid serves to prevent unfiltered donated stool from splattering or, otherwise, undesirably entering the extraction portion of the collection chamber.

The various apparatuses and components described above may be manufactured in different manners For example, in one embodiment, part or all of the collection chamber is formed using injection molding, 3D printing, or other processes. Similarly, part or all of the toilet mount may be formed using injection molding, 3D printing, or other processes. In particular, apart from the filter lid 107 and the collection chamber lid 8, the entire collection chamber, including an interior, porous wall (i.e., filter perforations and all) comprising the extraction portion, can be produced conveniently by an injection molding process, for example as a single piece.

Materials and Methods

The various embodiments of the fecal collection device described herein are designed to accomplish the same goal of collecting stool from a donor using the collection chamber, optionally filtering the stool before or after (or both) being mixed with an aqueous carrier, like water or saline, and allowing the aqueous stool mixture to be harvested from the collection chamber using an extraction/delivery device, such as a large syringe. The stool slurry thus produced can be used for fecal bacteriotherapy or other stool collection/transfer regimen. The methods described herein—after the stool is deposited into the collection chamber and, subsequently, sealed—are accomplished in a "closed" system, thereby obviating the need for transferring the stool from one container to another container, perhaps to a third container and so on and so forth. Once the donated stool is sealed inside the collection chamber using, for example, a water-tight lid, the person entrusted with processing and harvesting the stool specimen will not have to necessarily see or handle the contents in an open container setting.

Accordingly a collection chamber cradle (shown, for example in FIGS. 3, 4, and 5A-5C) is suspended inside a toilet using a brim placed across a toilet seat. An open collection chamber (e.g., 1, FIG. 1 and others) is then placed inside the cradle. The donor defecates into the open collection chamber, which can then be sealed using a cover (e.g., 8, FIGS. 1 and 2). Optionally the donor may add a predetermined volume of an aqueous solution to the stool specimen prior to sealing the contents of the collection chamber.

In some embodiments, the donated stool lands on the sieve platform (e.g., 4, FIG. 1). In this embodiment, if the stool is liquid, the majority will fall to the bottom of the collection chamber. The remaining, more solid stool may soften and fall as it combines with water or saline. One or more metal mixing balls (e.g., 13, FIG. 8) and/or one or more other agitators (e.g., 104, FIG. 10B) can be used to aid the breakdown of harder or more solid portions of the stool.

If not already present in the collection device, water, saline, or other aqueous carrier is introduced into the collection chamber using, for example, a cannula or large syringe via a port (i.e., an inlet/outlet), preferably a two-way or three-way stopcock (e.g., 6). As depicted in FIG. 1 a magnetic stirring platform may be activated, thereby causing a magnetic stirrer or stirring rod (e.g., 7) to spin and help create as slurry of liquid stool. Instead of the magnetic stirring rod, the metal mixing balls (e.g., 13, FIG. 8) may be formed of magnetic material and may mix the stool in response to the magnetic stirring platform being activated. Syringes may then be connected to the port, optionally equipped with a wide-gauge needle, to harvest the stool slurry. In certain embodiments, stool that is recovered first passes through a filter (e.g., 5, FIG. 1; 12, FIG. 7; 102, FIGS. 10A-10C), which may be hemispherical filter screen, a flat or rounded filter, or any other filter that is formed of a porous wall that thereby inhibits larger solid particles from clogging the syringe.

FIGS. 10D-10G depict additional features of a collection chamber, according to certain disclosed embodiments. As can be seen in these figures, an exemplary collection chamber may include a lip 108 which may assist in assuring full coverage of the filter 102, a snap-on portion 109, which may allow the filter lid 107 to securely close, notches 110 for securing the filter lid 107, a toilet mount locator 111 having, for example, a V shape, and fill lines 112, which may be used to assist a donor in dumping in the right amount of stool. In one embodiment, the filter lid 107 may have both a slanted and curved shape, to better protect the extraction chamber.

Figure 8:
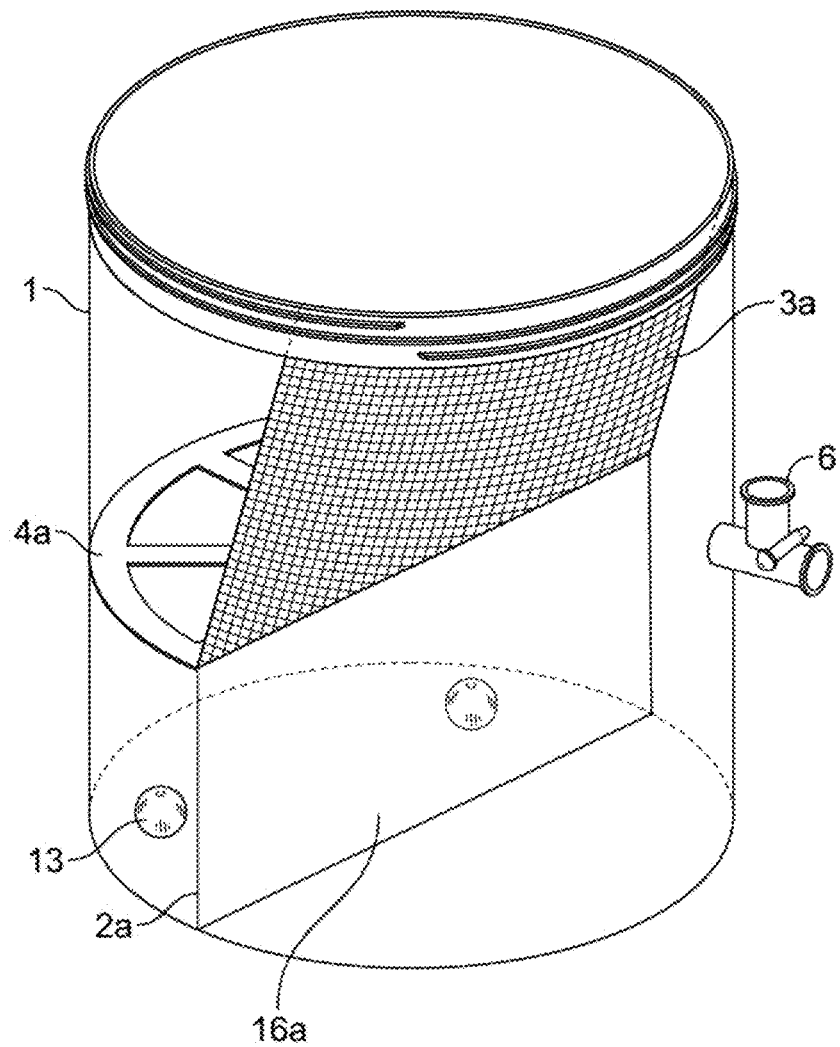
FIG. 8 illustrates an exemplary collection chamber (1) having a divider (2) comprised of a bottom solid wall (16), and a top porous wall comprising a screen filter (3) positioned diagonally, according to one exemplary embodiment. Also shown is a pair of exemplary metal balls (13) located in one compartment of the collection chamber.
Figure 9:
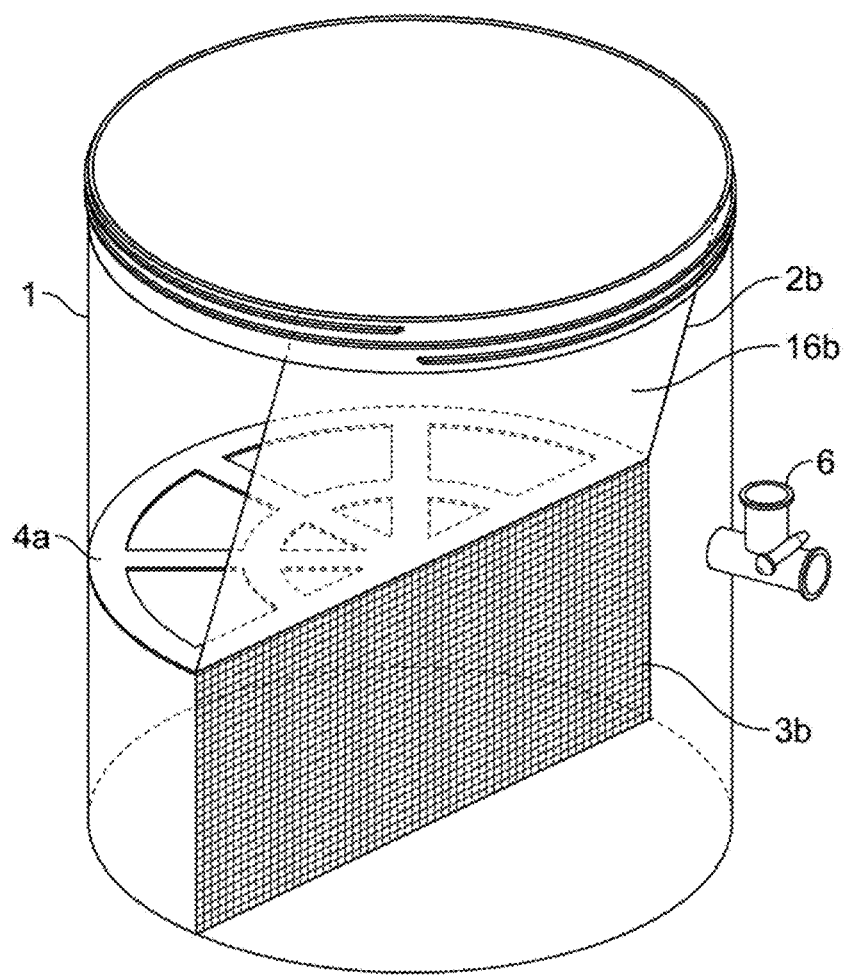
FIG. 9 shows an exemplary collection chamber (1) similar to that depicted in FIG. 8 except it does not include balls (13) and the divider (2) is comprised of a bottom porous wall comprising a screen filter (3) and a top solid wall (16) positioned diagonally.

As can be appreciated from the drawings accompanying this disclosure, the collection device in various embodiments described herein is divided into two or more compartments by a sieve and/or screen filter platform and/or a divider or dividing wall. The divider or dividing wall may further comprise a solid wall portion and a porous wall or dividing wall screen filter. A divider or dividing wall may be further equipped with lid, such as a solid semicircular top or flap, which separates that portion or compartment of the collection chamber which will eventually hold the stool slurry prior to recovery using a syringe or some other extraction device. Other embodiments of the divider or dividing wall are apparent from the various drawings. A two-part divider is shown in FIG. 8, with a substantially vertical solid wall (e.g., 16) and an angled, scooped porous or dividing wall screen filter (e.g., 3). As shown in FIG. 8, a semicircular sieve (4a) platform may be positioned at or about the junction of the solid and porous walls. However, the sieve is not necessary, and may be omitted. FIG. 9 depicts the divider of FIG. 8, except that a porous wall occupies the lower or bottom end of the collection chamber, while a solid wall occupies the top end. Again, a semicircular sieve may or may not be included with this divider.

On addition of saline or water either from by the donor or the person processing the stool specimen, the mixture is allowed to sit, preferably with swirling, to allow for the stool to soften. The contents of the collection chamber can manually agitated to increase mixing. In certain of the embodiments described above, the collection chamber is then tilted at a slight to severe angle to allow passage of liquid stool across the dividing wall screen filter (e.g., 3) into the compartment of the collection chamber equipped with an inlet/outlet port. The stool slurry is then recovered as described, above.

Specific Example 1

One example of a use of the disclosed stool collection apparatus is described as follows. A plastic cradle (or hat) is placed across the toilet with the toilet seat in the "up" position. The lid is removed from the collection device, and the open collection device is placed into the cradle, while aligning a "front" portion of the collection device with a "front" notch of the cradle. The toilet seat is lowered to the "down" position.

The donor, previously tested for infectious pathogens using a standard protocol and testing negative for same, sits down on the toilet, over the collection device opening and passes stool into the open collection device. There are optional markings on the inside wall of the collection device to give the donor a visual indication of optimal amounts of stool sample and/or a carrier medium, such as saline solution. Without being held to theory, it is believed that an optimal amount of stool sample ranges from about 25 gm to about 75 gm, preferably, about 50 gm. An appropriate amount of carrier solution can be added to the collection device to assist in the preparation of a slurry, which can then be withdrawn from a sealed collection device without necessitating that an operator remove and replace the lid one or more times (unless the operator purposefully desires to open the sealed collection device) during the preparation of a slurry within the sealed collection device, its filtration within the sealed collection device and its withdrawal from the collection device. A carrier medium, such as sterile saline solution, can be added prior to sealing the collection device. The carrier medium can also be added using one of the available inlet/outlet ports of the collection device, for example, the one positioned on top of the lid. The collection device is sealed prior to shipment, transport, or other transfer to a medical practitioner who can perform a fecal microbiota transplantation (FMT) procedure. Adjustments to the amounts of stool sample provided or administered and the amounts of carrier solution used to prepare a stool slurry can be made, as would be readily apparent to one of ordinary skill in the art.

In one embodiment of a process of making a stool slurry, 500 mL of non-bacteriostatic saline is added via a luer lock port positioned on the top of the lid, which is used to seal the collection device. Alternatively, as stated above, saline or water or other appropriate carrier medium or mixture can be added prior to sealing the collection device.

Once sealed with the appropriate amount of stool and carrier present inside, the collection device is agitated to create a suspension or slurry of stool. A first syringe, such as 5-mL syringe is anchored to the luer lock port positioned on the top of the lid, and the plunger is removed leaving only the barrel attached to the port to create a vent to facilitate aspiration. A second syringe, such as a 60-mL syringe (preferably, disposable) is anchored to a luer lock port positioned on a side of the sealed collection device and a "liquefied" donor stool suspension or slurry is aspirated into the syringe. One or more syringes can be pre-loaded, as desired by the medical practitioner, in preparation for a forthcoming FMT procedure.

In a particular embodiment of a FMT procedure, a total of ten (10) 60-mL syringes are pre-loaded. Blunt tip needles are attached to each syringe to facilitate use of a colonoscope to transfer the stool slurry or suspension from a syringe into a patient's gastrointestinal tract.

A patient is prepped and sedated for routine colonoscopy. A distal end of a colonoscope is inserted into the rectum of the patient and "worked" through a length of the patient's colon. Once the distal end of the colonoscope reaches a portion of the cecum, for example, the syringes are deployed with no resistance or clogging into the patient's colon. After the procedure the patient is allowed to recover not unlike any other conventional colonoscopic procedure.

Example of Actual Use

A patient, a 66 year old female initially presenting in with documented *C. diff* colitis, is prepped and sedated for routine colonoscopy. A distal end of a colonoscope is inserted into the rectum of the patient and "worked" through a length of the patient's colon. Once the distal end of the colonoscope reaches a portion of the cecum, for example, the syringes are deployed with no resistance or clogging into the patient's colon. After the procedure the patient is allowed to recover not unlike any other conventional colonoscopic procedure.

Prior to undergoing the FMT procedure, the patient suffered from severe diarrhea, cramps and weakness. Over some period of time, the patient had been subjected to oral vancomycin treatment, metronidazole treatment, back on vancomycin treatment, but the patient continued to suffer from loose, frequent and bloody stools. Additional treatment included oral Flagyl, then Fidaxamicin, but negative symptoms recurred soon after treatment regimen was completed.

After the FMT procedure the patient was observed in the recovery room for 60 minutes and then discharged to return home on a regular diet. After four days the patient called to report that her diarrhea was non-existent but that some mild cramps and gassiness persisted.

Thus, the utility of the claimed system has been demonstrated in which collection, processing and "delivery" of the stool sample is conducted in and from the same container. One of ordinary skill will recognize that "delivery" of the stool sample can be effected in any number of ways in addition to use of standard syringes and colonoscopes, including but not limited to, use of a nasogastric tube or a rectal tube affixed directly or indirectly to the disclosed apparatus.

Other embodiments of the disclosed apparatus will become apparent to those of ordinary skill in the art taking into consideration the descriptions and provided herein, which should not be construed to limit the disclosed invention in any manner inconsistent with the terms of the claims that immediately follow.

What is claimed is:

1. An apparatus for the collection of donated stool comprising a collection chamber and a cradle configured to suspend the collection chamber within a toilet bowl, the collection chamber comprising:
   (a) a hollow cylindrical drum equipped with a closed bottom and a removable cover to expose an interior of the drum from a top;
   (b) a divider positioned vertically and/or diagonally within the drum's interior to divide the drum's interior into at least two compartments, the divider comprising a porous wall; and
   (c) one or more ports, which can serve as an inlet, an outlet, or both, provided that at least one of the at least two compartments is fitted with at least one port, the one or more ports including a port on the drum,
   wherein the removable cover is shaped to attach to a top of the drum, and to enclose the interior of the drum,
   wherein the porous wall extends from a first height within the drum's interior to a second height within the drum's interior, and
   wherein the porous wall comprises a screen filter.

2. The apparatus of claim 1, wherein the port on the drum comprises a two-way stopcock.

3. The apparatus of claim 1 in which the cradle comprises a brim that sits over a toilet seat providing a profile similar to an upside down brimmed hat.

4. The apparatus of claim 1 in which the cradle comprises two U-shaped brackets.

5. The apparatus of claim 1 in which the divider is positioned vertically, dividing the drum's interior into a first compartment and a second compartment, the divider comprising a combination of the porous wall and a solid wall.

6. The apparatus of claim 5 in which the lower portion of the divider is the solid wall.

7. The apparatus of claim 1 in which the divider comprises a lower vertical solid wall and the porous wall, which is an upper porous wall positioned diagonally from a topmost portion of the vertical solid wall towards a topmost portion of the drum, dividing the drum's interior into a first compartment and a second compartment.

8. The apparatus of claim 7 in which the first compartment further comprises a planar semicircular sieve positioned orthogonally at the topmost portion of the vertical solid wall.

9. The apparatus of claim 1 in which the divider comprises a lower vertical porous wall as the screen filter, and an upper solid wall positioned diagonally from a topmost portion of the lower vertical porous wall towards a topmost portion of the drum, dividing the drum's interior into a first compartment and a second compartment.

10. The apparatus of claim 9 in which the second compartment is fitted with a port comprising a two-way stopcock.

11. The apparatus of claim 1, wherein the divider separates the collection chamber into a collection portion and an extraction portion, and further comprising:
   a lid covering the extraction portion and having a slanted angle.

12. The apparatus of claim 1, wherein the cradle includes foldable wings.

13. A collection chamber for depositing, processing and harvesting stool from a donor comprising:
   (a) a hollow cylindrical drum equipped with a closed bottom and a removable cover to expose an interior of the drum from a top;
   (b) a divider positioned vertically and/or diagonally within the drum's interior to divide the drum's interior into at least two compartments, the divider comprising a porous wall or a combination of a porous wall and a solid wall;
   (c) one or more ports, which can serve as an inlet, an outlet, or both, provided that at least one of the at least two compartments is fitted with at least one port; and
   (d) a plurality of agitators formed of a plurality of spike-shaped protrusions at a bottom of the drum in a collection portion,
   wherein the plurality of agitators and at least the bottom of the drum are formed of a single molded piece.

14. The collection chamber of claim 13, wherein the divider divides the drum into a collection portion and an extraction portion, and further comprising:
   a port connected to the extraction portion.

15. The collection chamber of claim 13, wherein the divider includes a solid wall connected to the porous wall.

16. An apparatus for the collection of donated stool comprising a collection chamber and a cradle configured to suspend the collection chamber within a toilet bowl, the collection chamber comprising:
   (a) a hollow cylindrical drum equipped with a closed bottom and a removable cover to expose an interior of the drum from a top;

(b) a divider positioned vertically and/or diagonally within the drum's interior to divide the drum's interior into at least two compartments, the divider comprising a porous wall; and (c) one or more ports, which can serve as an inlet, an outlet, or both, provided that at least one of the at least two compartments is fitted with at least one port, the one or more ports including a port on the drum, wherein the removable cover is shaped to attach to a top of the drum, and to enclose the interior of the drum, wherein the porous wall extends from a first height within the drum's interior to a second height within the drum's interior, and wherein the divider includes a solid wall connected to the porous wall.

17. The apparatus of claim 16, wherein the solid wall also extends from the first height to the second height.

18. An apparatus for the collection of donated stool comprising a collection chamber and a cradle configured to suspend the collection chamber within a toilet bowl, the collection chamber comprising:

(a) a hollow cylindrical drum equipped with a closed bottom and a removable cover to expose an interior of the drum from a top;

(b) a divider positioned vertically and/or diagonally within the drum's interior to divide the drum's interior into at least two compartments, the divider comprising a porous wall; and (c) one or more ports, which can serve as an inlet, an outlet, or both, provided that at least one of the at least two compartments is fitted with at least one port, the one or more ports including a port on the drum, wherein the removable cover is shaped to attach to a top of the drum, and to enclose the interior of the drum, wherein the porous wall extends from a first height within the drum's interior to a second height within the drum's interior, and wherein:

the divider separates the collection chamber into a collection portion and an extraction portion; and the port on the drum connects to the extraction portion.

19. The apparatus of claim 18, further comprising:

a plurality of agitators at a bottom of the drum in the collection portion.

20. The apparatus of claim 19, wherein the plurality of agitators are affixed to a bottom of the drum.

21. A collection chamber for depositing, processing and harvesting stool from a donor comprising:

(a) a hollow cylindrical drum equipped with a closed bottom and a removable cover to expose an interior of the drum from a top;

(b) a divider having a vertical portion and a diagonal portion within the drum's interior to divide the drum's interior into at least two compartments including a collection portion and an extraction portion, the divider comprising at least a porous wall;

(c) at least a first port on the drum, which port can serve as an inlet, an outlet, or both, the first port located on the extraction portion of the drum.

22. The collection chamber of claim 21, wherein:

the porous wall corresponds to one of the vertical portion and the diagonal portion of the divider; and the other one of the vertical portion and the diagonal portion of the divider comprises a solid wall.

23. The collection chamber of claim 21, wherein:

the drum and at least the vertical portion of the divider are formed of a single molded piece.

24. The collection chamber of claim 23, further comprising:

a plurality of agitators at the bottom of the drum, wherein the plurality of agitators are formed of the same molded piece as the drum and divider.

* * * * *